(12) United States Patent
McGregor et al.

(10) Patent No.: US 6,942,874 B2
(45) Date of Patent: Sep. 13, 2005

(54) NUCLEOTIDE COMPOUNDS THAT BLOCK THE BITTER TASTE OF ORAL COMPOSITIONS

(75) Inventors: Richard Alexander McGregor, Rutherford, NJ (US); Stephen Anthony Gravina, Rutherford, NJ (US)

(73) Assignee: Linguagen Corp., Cranbury, NJ (US)

( * ) Notice: Subject to any disclaimer, the term of this patent is extended or adjusted under 35 U.S.C. 154(b) by 82 days.

(21) Appl. No.: 09/865,346

(22) Filed: May 25, 2001

(65) Prior Publication Data

US 2002/0177576 A1 Nov. 28, 2002

(51) Int. Cl.[7] .................................................. A61K 47/00
(52) U.S. Cl. .......................... 424/439; 514/23; 514/42; 514/45; 514/49
(58) Field of Search ............................ 424/439; 514/23, 514/42, 45, 46, 47, 49

(56) References Cited

U.S. PATENT DOCUMENTS

| | | | |
|---|---|---|---|
| 4,243,691 A | 1/1981 | Mohlenkamp, Jr., et al. | |
| 5,232,735 A | 8/1993 | Kurtz et al. | |
| 5,631,038 A | 5/1997 | Kurtz et al. | |
| 5,631,231 A | 5/1997 | Kurtz et al. | |
| 5,631,232 A | 5/1997 | Kurtz et al. | |
| 5,631,240 A | 5/1997 | Kurtz et al. | |
| 5,631,252 A | 5/1997 | Kurtz et al. | |
| 5,631,272 A | 5/1997 | Kurtz et al. | |
| 5,631,292 A | 5/1997 | Kurtz et al. | |
| 5,631,294 A | 5/1997 | Kurtz et al. | |
| 5,631,295 A | 5/1997 | Kurtz et al. | |
| 5,631,299 A | 5/1997 | Kurtz et al. | |
| 5,637,618 A | 6/1997 | Kurtz et al. | |
| 5,639,788 A | 6/1997 | Kurtz et al. | |
| 5,641,795 A | 6/1997 | Kurtz et al. | |
| 5,641,799 A | 6/1997 | Kurtz et al. | |
| 5,641,811 A | 6/1997 | Kurtz et al. | |
| 5,641,812 A | 6/1997 | Kurtz et al. | |
| 5,643,894 A | 7/1997 | Kurtz et al. | |
| 5,643,941 A | 7/1997 | Kurtz et al. | |
| 5,643,945 A | 7/1997 | Kurtz et al. | |
| 5,643,955 A | 7/1997 | Kurtz et al. | |
| 5,643,956 A | 7/1997 | Kurtz et al. | |
| 5,646,122 A | 7/1997 | Kurtz et al. | |
| 5,650,403 A | 7/1997 | Kurtz et al. | |
| 5,654,311 A | 8/1997 | Kurtz et al. | |
| 5,665,755 A | 9/1997 | Kurtz et al. | |
| 5,700,792 A | 12/1997 | Kurtz et al. | |
| 5,703,053 A | 12/1997 | Kurtz et al. | |
| 5,853,792 A | 12/1998 | Zolotov et al. | |
| 5,866,608 A | 2/1999 | Kurtz et al. | |
| 6,008,250 A | 12/1999 | Kurtz et al. | |
| 6,015,792 A | 1/2000 | Kurtz et al. | |

FOREIGN PATENT DOCUMENTS

| | | | |
|---|---|---|---|
| EP | 0 059 363 | 12/1984 | |
| EP | 0 122 400 | 7/1987 | |
| EP | 0 125 021 | 7/1987 | |
| EP | 0 416 667 B1 | 9/1993 | |
| JP | S48-17044 | * 5/1973 | |
| JP | 11-169131 | * 6/1999 | ............ A32L/1/229 |

OTHER PUBLICATIONS

Adler et al.; 2000; Cell, vol. 100 pages 639–702.
Amer and Kreighbaum; 1975; Journal of Pharmaceutical Sciences, vol. 64, pp. 1–35.

(Continued)

*Primary Examiner*—Thurman K. Page
*Assistant Examiner*—Konata M. George
(74) *Attorney, Agent, or Firm*—Sterne, Kessler, Goldstein & Fox P.L.L.C.

(57) ABSTRACT

Nucleotides that block the bitter taste of foods, beverages, pharmaceutically active oral dose preparations, cosmetics and other bitter compounds that come into contact with taste tissue. The nucleotides consist of a purine or pyrimidine group, or derivative thereof, and an ionizable phosphate or other anionic organic molecule.

9 Claims, 8 Drawing Sheets

OTHER PUBLICATIONS

Figure 2A:
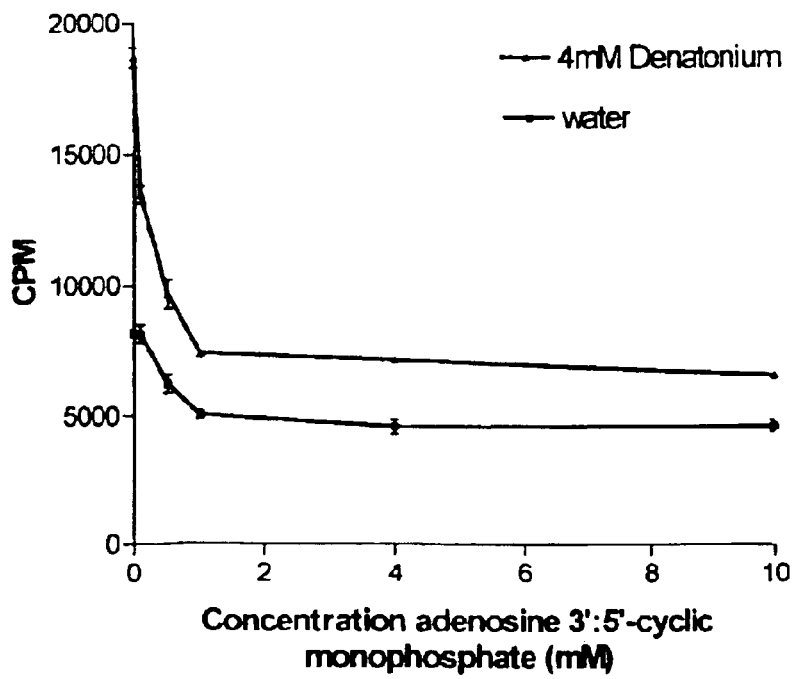
Figure 2B:
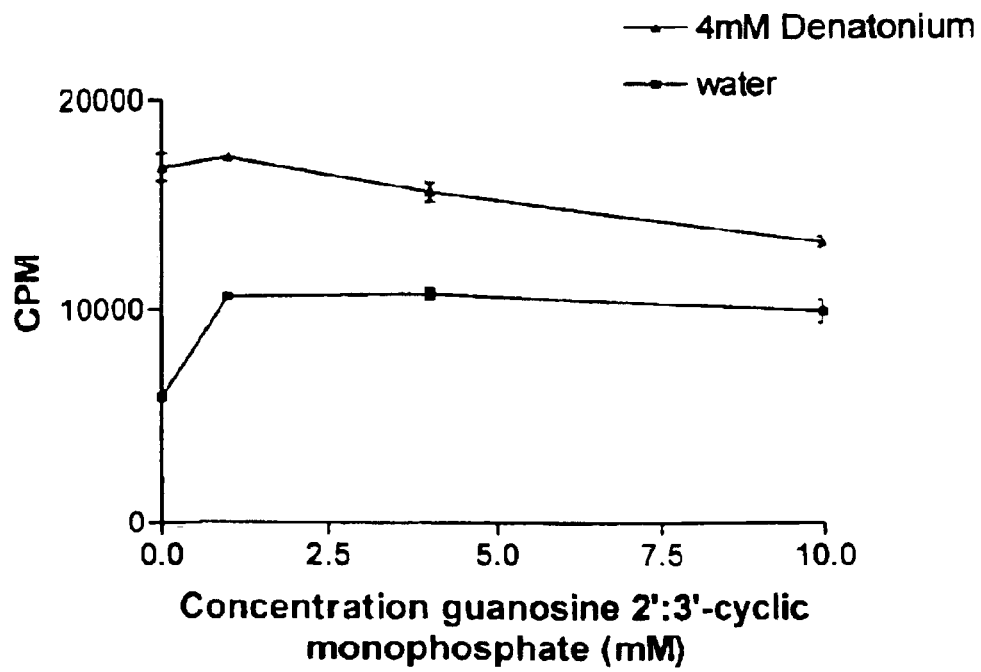
Figure 2C:
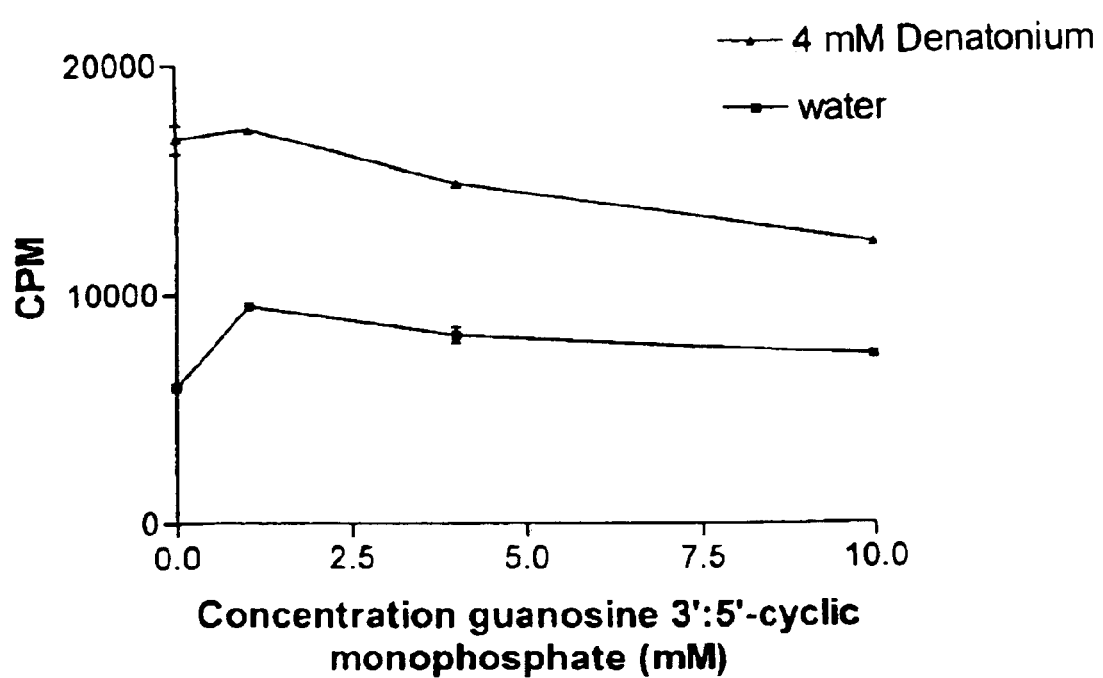
Figure 2D:
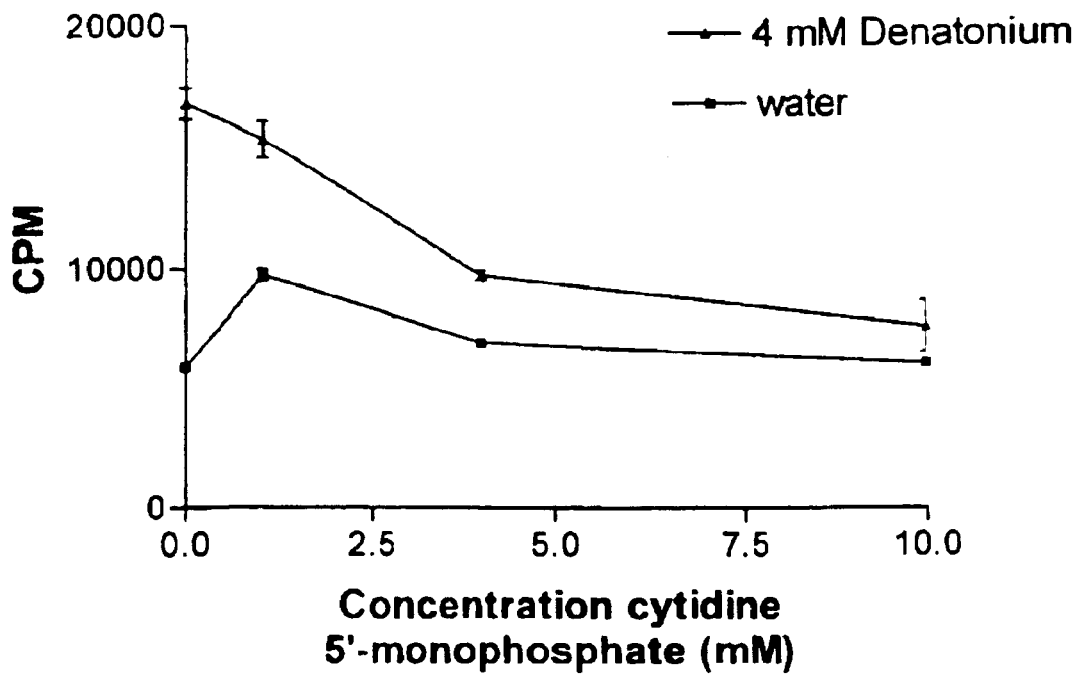
Figure 2E:
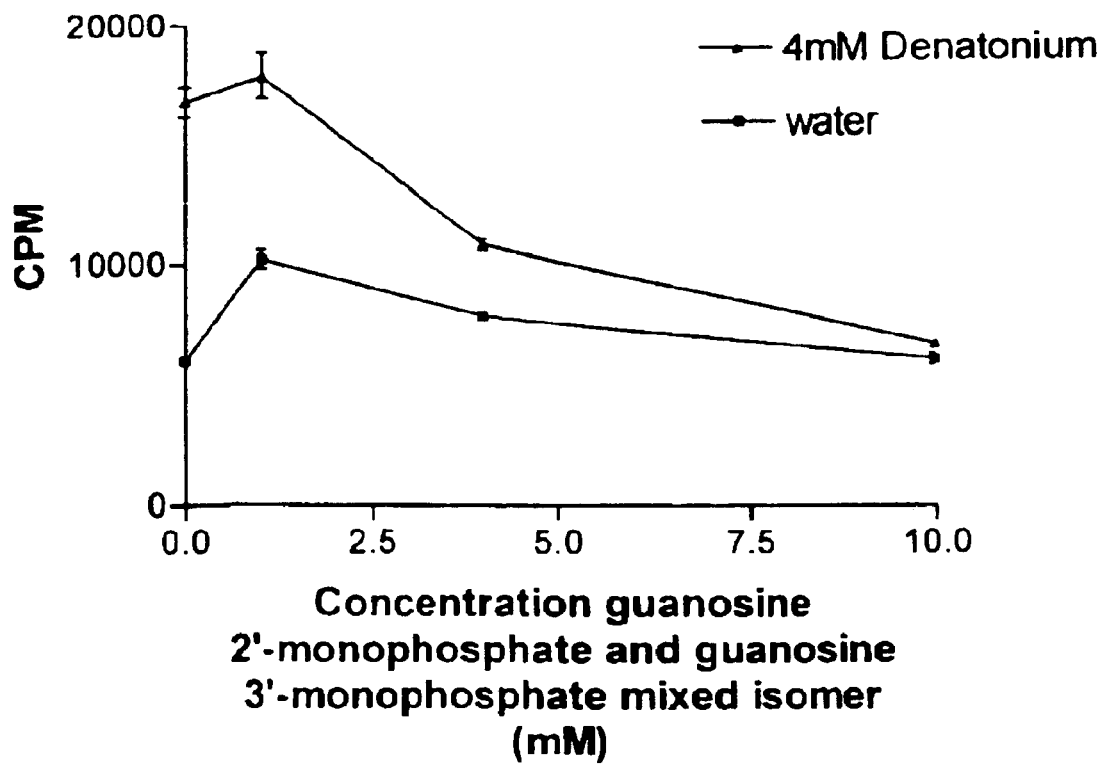
Figure 2F:
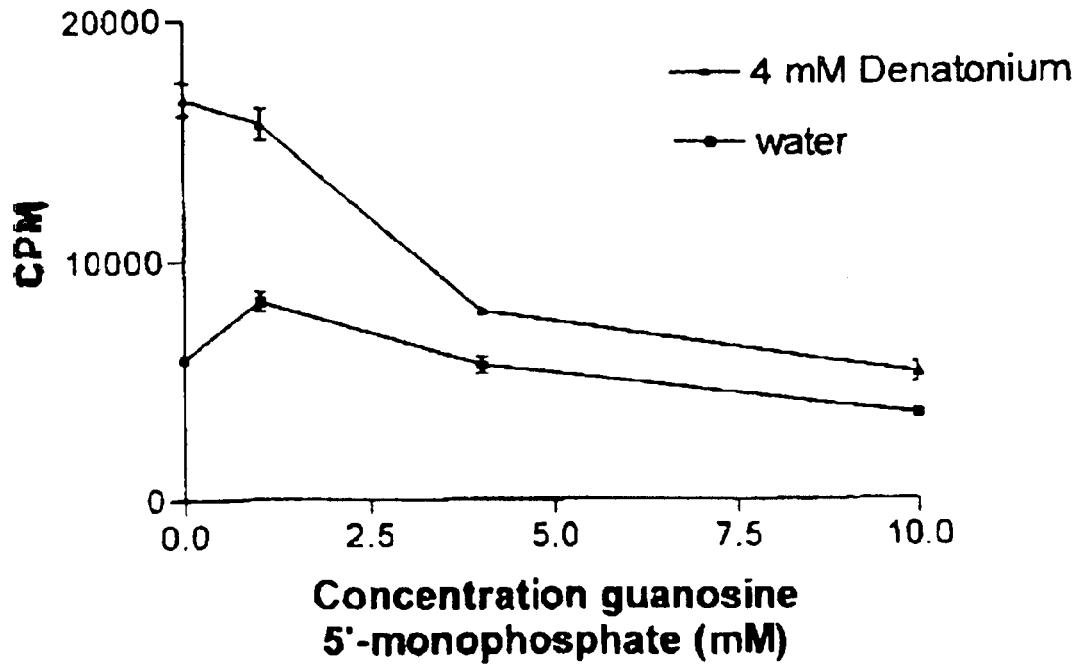
Figure 2G:
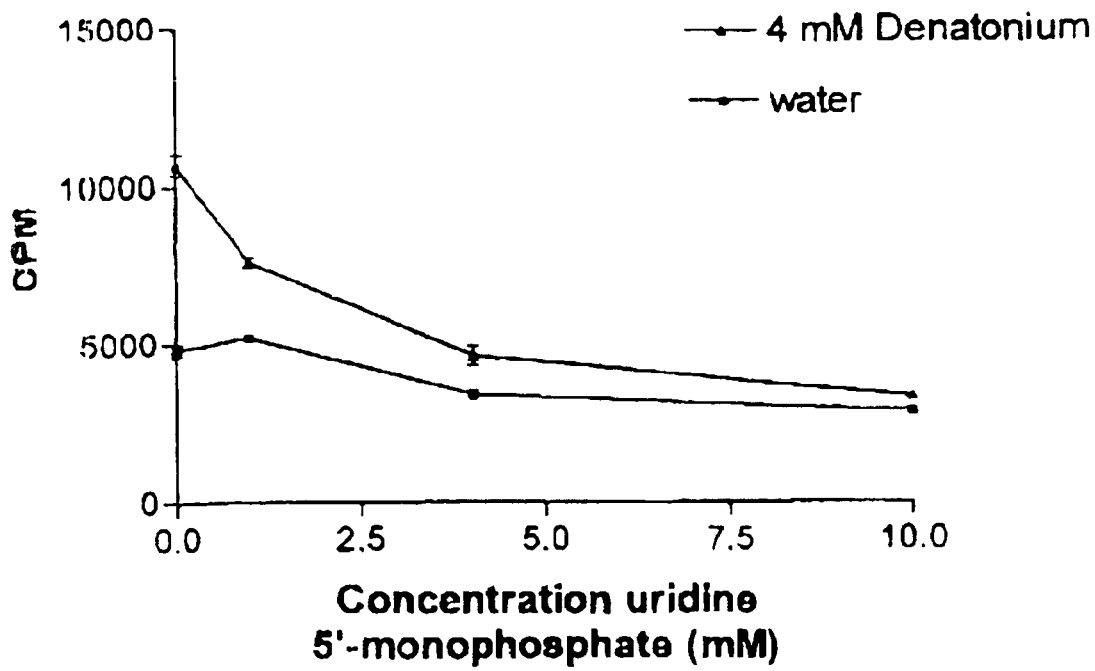
Figure 2H:
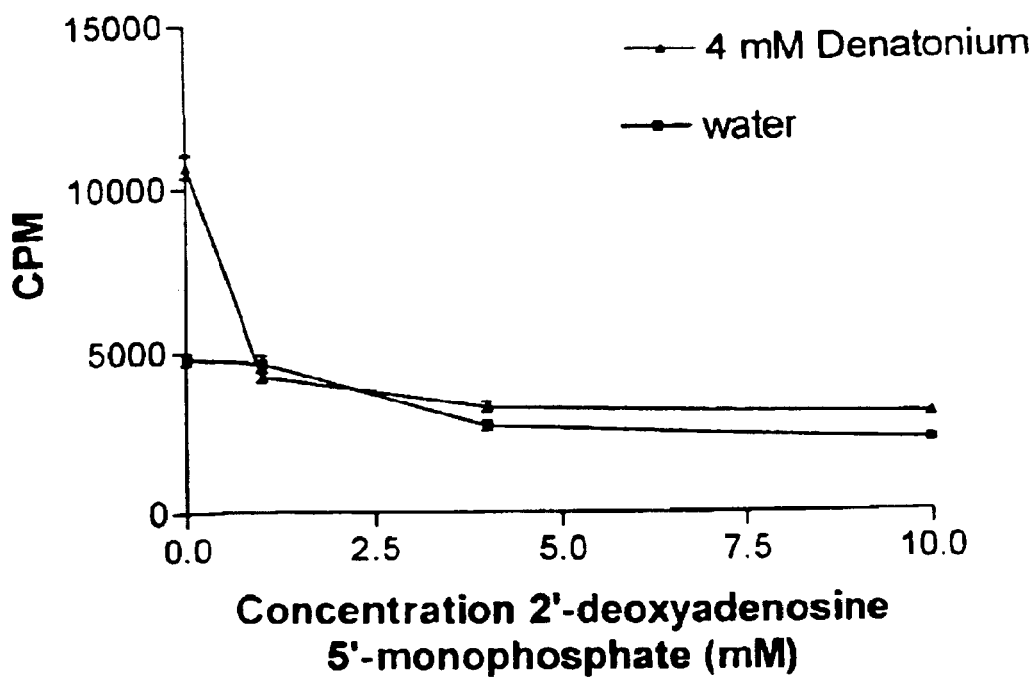
Figure 2I:
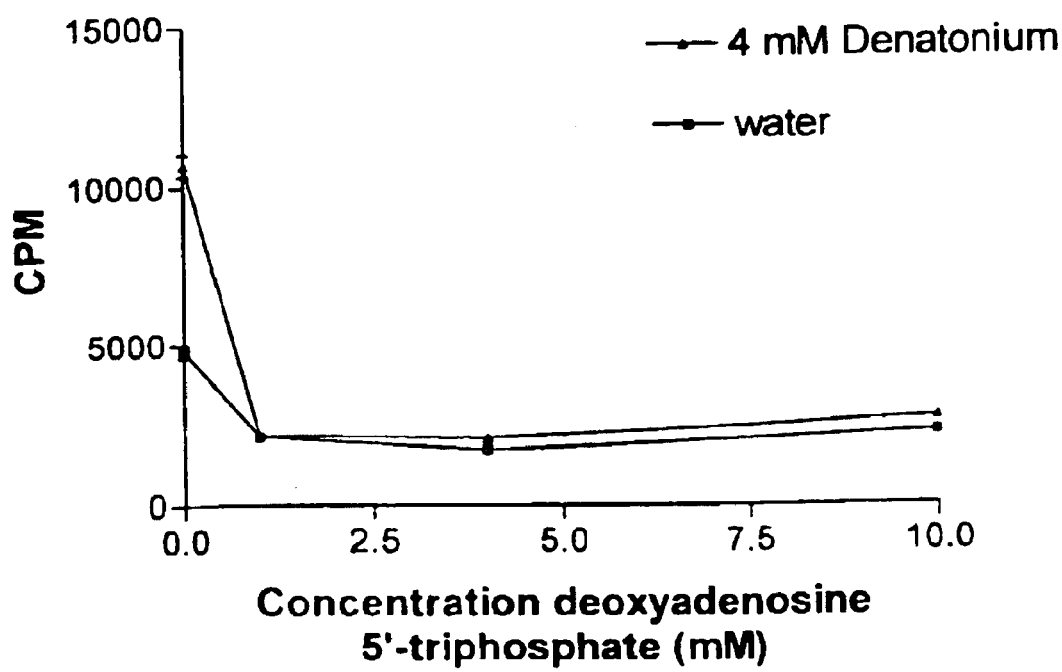
Figure 2J:
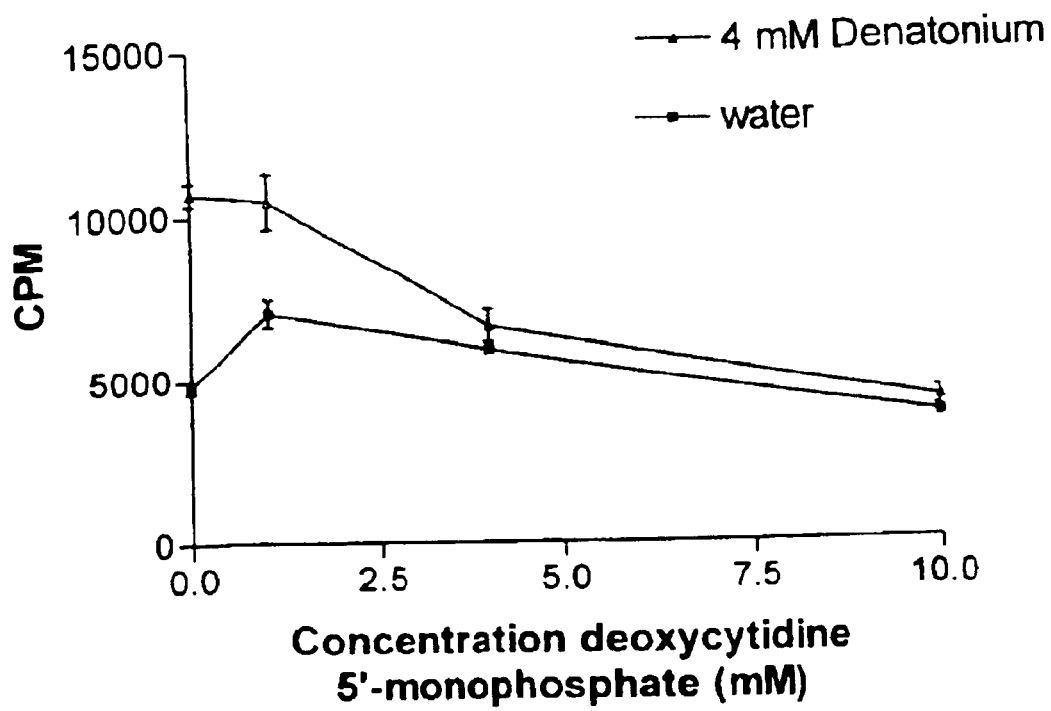
Figure 2K:
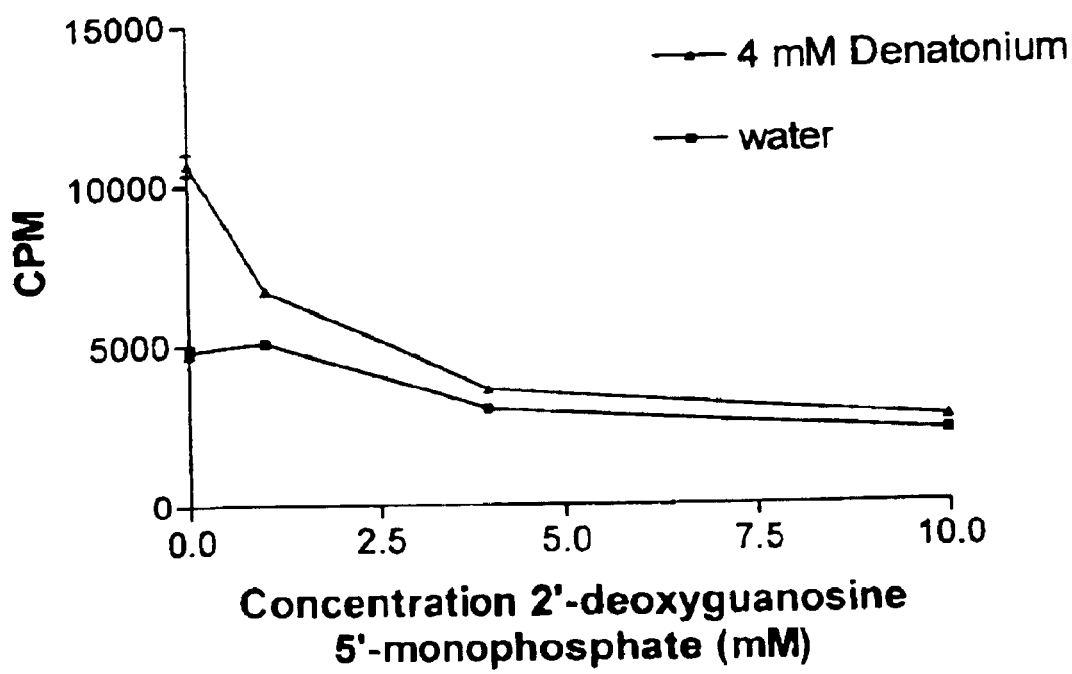

Asano et al.; 1984; Biochemistry; vol. 23 pp. 5460–5467.
Birnbaumer et al.; 1990; Biochimica et Biophysica Acta, vol. 1031, pp. 163–224.
Chandrashekar et al.; 2000; Cell; vol. 100, pp. 703–711.
Gilbertson et al.; 2000; Current Opinion in Neurobiology; vol. 3, pp. 519–527.
McGregor and Gravina; 2001; 23rd Meeting of Association of Chemoreceptor Science.
Hoon et al.; 1995; Biochem J.; vol. 309, pp. 629–636.
Huang et al.; 1999; Nature Neuroscience; vol. 2, pp. 1055–1062.
Matsunami et al.; 2000; Nature; vol. 404, pp. 601–604.
Margolskee et al.; 1993; Current Opinion in Neurobiology; vol. 3, pp. 526–531.
Margolskee et al.; 1993; BioEssays; vol. 15, pp. 645–650.
Ming et al.; 1999; Proc. Natl. Acad. Sci. USA; vol. 96, pp. 9903–9908.
Ming et al.; 1998; Proc. Natl. Acad. Sci. USA; vol. 95, pp. 8933–8938.
Gravina et al.; 2001; in preparation; p. 4 of spec.
McLaughlin et al.; 1992; Nature; vol. 357, pp. 563–569.
Naim et al.: 1994; Biochem J.; vol. 297, pp. 451–454.
Rarick et al.; 1992; Science; vol. 256, pp. 1031–1033.
Rodbell et al.; 1971; The Journal of Biological Chemistry; vol. 246, pp. 1877–1882.
Ruiz–Avila et al.; 1995; Nature; vol. 376, pp. 80–85.
Ruiz–Avila et al.; 2000; Chem Senses; vol. 25, pp. 361–368.
Spielman et al.; 1994; Physiology and Behavior; vol. 56, pp. 1149–1155.
Wong et al.; 1996; Nature; vol. 381, pp. 796–800.
Tsunenari et al.; 1999; Journal of Physiology; vol. 519.2, pp. 397–484.
Dialog File 351, Accession No. 3529012, Derwent WPI English language abstract for EP 0 059 363.

* cited by examiner

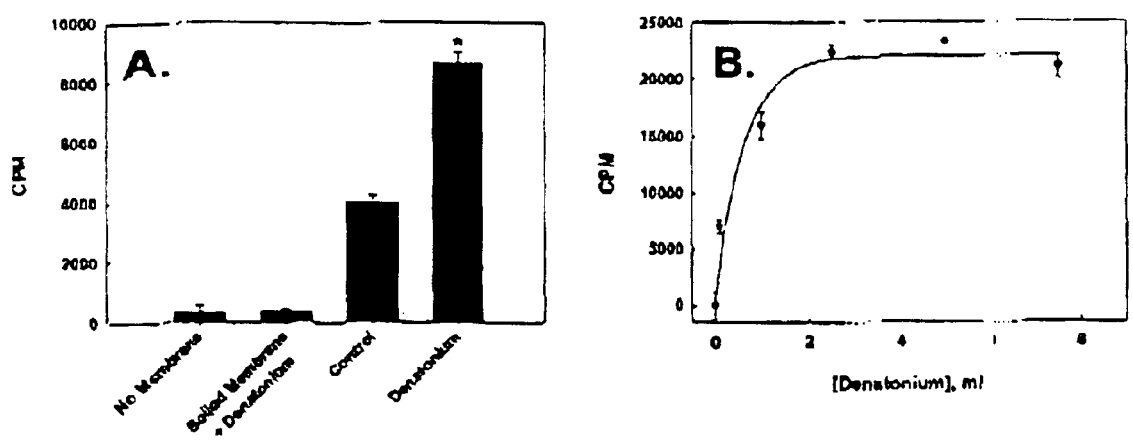
Figure 1A-B

NUCLEOTIDE COMPOUNDS THAT BLOCK THE BITTER TASTE OF ORAL COMPOSITIONS

1. INTRODUCTION

The present invention relates to methods and compositions for inhibiting the sensory perception of bitterness. The inhibitors of the invention may be used as flavor enhancers in foods and pharmaceuticals. The present invention is based, at least in part, on the discovery that nucleotide compounds are capable of inhibiting the activation of G-proteins involved in the perception of bitterness.

2. BACKGROUND OF THE INVENTION

The sense of taste can be divided into five predominant categories: bitter, salty, sour, sweet and umami. Taste perception begins with the interaction of sapid molecules (tastants) with taste receptor cells, which reside in specialized structures known as taste buds (Margolskee et al., 1993, Bioessays 15:645–50; Margolskee et al., 1993, Current Opin Neurobiol. 3:526–31). Taste buds are located in the papillae of the tongue and are the end organ of taste. The function of the taste buds is to relay information on the nutrient content of food to the central nervous system through afferent gustatory fibers. Recent advances in the molecular biology and biochemistry of taste have shown that each taste modality affects receptor cells through distinct mechanisms (Gilbertson et al., 2000 Curr Opin Neurobiol 10:519–27). Transduction of responses to bitter and sweet compounds are predominantly mediated via guanine nucleotide binding protein (G protein) coupled receptors, while salty and sour responses involve interactions with ion channels.

Gustducin is a taste selective G protein (McLaughlin et al., 1992 Nature 357:563–9). Gustducin is homologous (~80% identical/~90% similar) to transducin, the G protein of the visual system, and both gustducin and transducin have been immunocytochemically localized to taste buds. In the retina, light activates rhodopsin, a member of the seven transmembrane-helical G protein coupled receptor family, resulting in a conformational change and activation of transducin. Transducin subsequently disinhibits a cyclic guanidine monophosphate (cGMP) specific phosphodiesterase (PDE) and the resultant decreased cGMP concentration leads to modulation of ion channel permeability causing rod cell hyperpolarization (Birnbaumer et al, 1990 Biochem, Biophys. Acta 1031:163–224). Because of gustducin's high degree of similarity to transducin, it is thought that gustducin may be involved in taste signal transduction by modulation of a taste specific PDE. This hypothesis is further supported by the fact that transducin's PDE activating domain is 86% identical and 95% similar to gustducin's, while other G proteins have much lower relatedness in this region (Rarick et al., 1992 Science 256:1031–3). Furthermore, recombinant gustducin expressed in SF9 cells has been shown to be activated by rhodopsin and can activate retinal and taste cGMP PDE (Hoon et al., 1995 Biochem J 309:629–36; Ruiz-Avila et al., 1995 Nature 376:80–5). Thus, gustducin and transducin appear to be interchangeable in this regard.

Transducin has also been immunocytochemically localized to taste buds, and has been implicated in taste signal transduction by activation of a taste specific PDE activity (Ruiz-Avila et al., 1995 Nature 376:80–5). Furthermore, this study and subsequent work (Ming et al., 1998 Proc Nat'l Acad Sci USA 95:8933–8) demonstrated that taste bud containing membranes from bovine circumvallate papillae activated exogenously added transducin in response to bitter stimuli including denatonium, quinine, strychnine, atropine and naringen.

Gustducin has been implicated in vivo in transducing responses to bitter and sweet compounds (Wong et al., 1996, Nature 381:796–800). Gene replacement was used to generate a null mutation of the α-gustducin gene in mice. The α-gustducin knockout mice were shown to be deficient in responses to both bitter and sweet compounds as measured by two bottle preference tests as well as electrophysiology. The gustducin knockout had no effect on responses to sour or salty compounds.

Recently, putative human and rodent taste receptors for bitter taste (the T2Rs) have been cloned and cells expressing certain of these clones demonstrated to respond to the bitter compounds denatonium, cyclohexamide and 6-n-propyl-2-thiouracil (PROP) (Hoon et al., 1995 Biochem J 309:629–36; Adler et al., 2000 Cell 100:693–702; Chandrashekar et al., 2000 Cell 100:703–11; Matsunami et al., 2000 Nature 404:601–4). The T2R receptors appear to be specifically expressed in only the α-gustducin positive taste receptor cells, consistent with their proposed role in bitter transduction.

Although gustducin- and transducin-mediated pathways appear to be the primary mechanism by which responses to bitter compounds are transduced, alternative mechanisms have also been proposed. Evidence thus far suggests that bitter taste transduction may be mediated by (1) G protein coupled receptors acting via gustducin/transducin (Ruiz-Avila et al., 1995 Nature 376:80–5; Wong et al, 1996; Ming et al., 1998 Proc Nat'l Acad Sci USA 95:8933–8; Gravina et al., 2001, in preparation). Our work and that of others suggest that at least 50% of bitter compounds couple through a receptor-dependent gustducin/transducin pathway; (2) G protein coupled receptors acting via Gq or βγ subunits to generate inositol triphosphate (Spielman et al., 1994 Physiol Behav 56:1149–55; Huang et al., 1999 Nat Neurosci 2:1055–62). A recently identified G protein γ subunit expressed in gustducin positive taste cells has been shown to mediate the response of certain bitter compounds to a phospholipase C (PLC) catalyzed increase in inositol triphosphate ($IP_3$) (Huang et al., 1999 Nat Neurosci 2:1055–62). This γ subunit is associated with gustducin in the taste cell. Other tastants appear to link via a different G protein (Gq) to $IP_3$ production (Spielman et al., 1994 Physiol Behav 56:1149–55); (3) Receptor independent effects of bitter tasting molecules acting directly on G proteins and effector proteins such as phosphodiesterase and ion channels (Naim et al., 1994 Biochem J 297:451–4; Amer and Kreighbaum, 1975 J. Pharm. Sci. 64:1–35; Tsunenari, 1999 J Physiol 519 Pt 2:397–404).

Traditionally, sweeteners and flavorants have been used to mask the bitter taste of pharmaceuticals. The sweetener or flavorant are known to activate other taste pathways and at sufficiently high concentration this serves to mask the bitter taste of the pharmaceutical. However, this approach has proved ineffective at masking the taste of very bitter compounds. Microencapsulation in a cellulose derivative has also been used to mask the bitter taste of pharmaceuticals, however this approach prevents rapid oral absorption of the pharmaceutical. The nucleotide monophosphates IMP and GMP have been used to counter the metallic or pseudo-bitter taste of KCl for its use in low sodium edible salt composition (Zolotov et al., U.S. Pat. No. 5,853,792). In addition, AMP has been described as an inhibitor of bitter taste (Ming et al., Proc. Natl Acad Sci USA 96:9903–8; McGregor and Gravina 2001, 23rd Meeting of the Association of Chemoreception Sciences).

3. SUMMARY OF THE INVENTION

The present invention relates to methods and compositions for inhibiting the sensory perception of bitterness. It is based, at least in part, on the discovery that nucleotide compounds and related chemical derivatives thereof are capable of inhibiting the activation of G-proteins by bitter tastant-stimulated taste receptors and result in behavioral responses which indicate that the sensation of bitterness is diminished.

Inhibitors of the invention may be used to decrease or abrogate the perception of bitterness of bitter tastants, in which capacity they are referred to as "bitterness inhibitors". In related embodiments, the present invention provides for methods of decreasing the perception of bitterness associated with a tastant by co-administering one or more bitterness inhibitors, and also provides for compositions comprising a bitter tastant and a bitterness inhibitor.

The inhibitors of the invention may be used to enhance the flavor of foods, beverages, and pharmaceuticals by decreasing or eliminating bitter taste features. In addition to increasing food consumer satisfaction, inhibitors of the invention may also permit the incorporation, into foods and pharmaceuticals, of bitter tastants that improve shelf-life or nutritive value. The inhibitors of the invention could increase food intake in humans or livestock. Moreover, inhibitors of the invention could render medical procedures involving bitter compositions more palatable, and improve compliance in drug regimens involving bitter tastants, particularly when administered to children.

The recent discovery of G protein pathways underlying bitter taste allows the use of biochemical and molecular biological approaches to discover potential bitter antagonists. Using these methods, nucleotide compounds have been identified that are claimed to block the bitter taste of bitter compounds, such as those found in pharmaceuticals, foods, beverages and cosmetics. These nucleotides may be incorporated into compositions of bitter tasting pharmaceuticals to improve compliance, or combined with bitter tasting compounds added to foods and beverages to improve nutritive value or shelf life.

The present invention relates to methods for blocking the bitter taste of oral compositions. The oral composition consists of a bitter tastant and may be of organic or inorganic elemental atoms. The blockade of bitter oral compositions can be accomplished with 0.01 to 20 mM of a nucleotide having the composition of nucleic acid, or chemical derivative of nucleic acid and ionizable phosphate or other anionic organic molecule. The nucleotide compounds identified in the claims block the bitter taste of oral compositions by inhibiting the activation of gustducin or transducin in an in vitro biochemical assay, and by blocking the bitter taste of oral compositions in an in vivo taste assay with human subjects.

4. BRIEF DESCRIPTION OF THE DRAWINGS

FIGS. 1A–B. Activation of Transducin by Bitter Compounds. (1A) Transducin has minimal binding of [$^{35}$S] GTPγS in the absence of membranes or when membranes were boiled for 5 minutes. (1B) Concentration dependent activation of transducin by denatonium in the presence of circumvallate membranes.

FIGS. 2A–K Inhibition of denatonium mediated transducin activation by nucleotide compounds.

Figure 3:
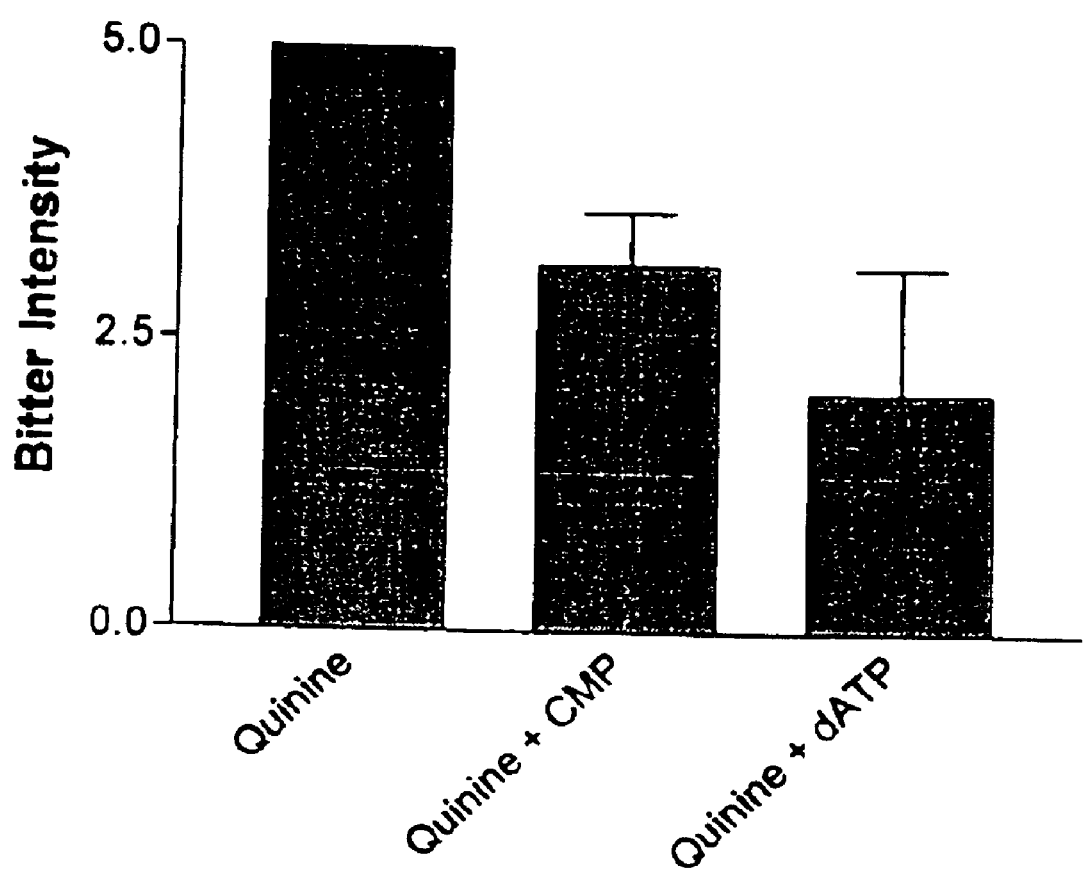

FIG. 3. In vivo taste assay in the presence of quinine, quinine+cytidine 5'-monophosphate (CMP) and quinine+2' deoxyadenosine 5'-triphosphate (dATP).

5. DETAILED DESCRIPTION OF THE PREFERRED EMBODIMENTS

The present invention provides for methods of inhibiting a bitter taste resulting from contacting a taste tissue of a subject with a bitter tastant, comprising administering to the subject an effective amount of a bitterness inhibitor, such as a bitterness inhibitor identified by measuring G-protein. The present invention also provides for methods of inhibiting a bitter taste of a composition, comprising incorporating, in the composition, an effective amount of a bitterness inhibitor. An "effective amount" of the bitterness inhibitor is an amount that subjectively decreases the perception of bitter taste and/or that is associated with a detectable decrease in G-protein activation as measured by one of the above assays.

The present invention is based on the discovery that nucleotide compounds and related chemical derivatives are capable of inhibiting bitter tastant mediated activation of G-proteins. In addition, in vivo taste assays were utilized by testing their activity using human subjects.

In specific, non-limiting embodiments of the invention, the bitterness inhibitor may be selected from the group consisting of adenosine 3':5'-cyclic monophosphate, guanosine 2':3'-cyclic monophosphate, guanosine 3':5'-cyclic monophosphate, cytidine 5'-monophosphate, guanosine 2'-monophosphate, guanosine 3'-monophosphate, guanosine 5'-monophosphate, uridine 5'-monophosphate, 2'-deoxyadenosine 5'-monophosphate, 2'-deoxyadenosine 5'-triphosphate, 2'-deoxycytidine 5'-monophosphate, and 2'-deoxyguanosine 5'-monophosphate.

The structures of such compounds are as follows:

Adenosine 3':5'-cyclic monophosphate

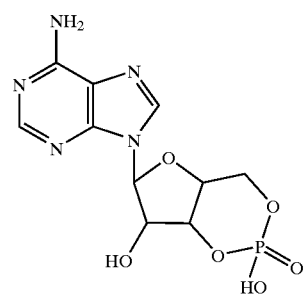

Guanosine 2':3'-cyclic monophosphate

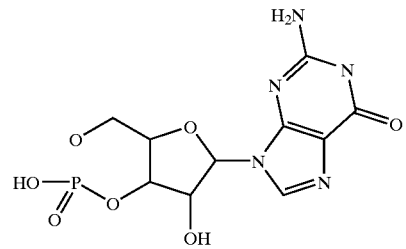

Guanosine 3':5'-cyclic monophosphate

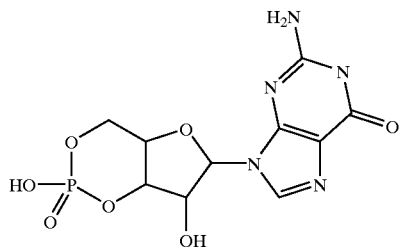

Cytidine 5'-monophosphate

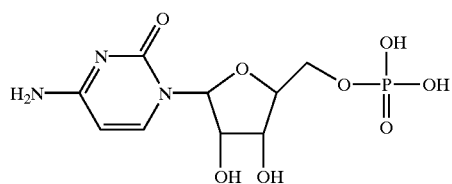

Guanosine 2'-monophosphate

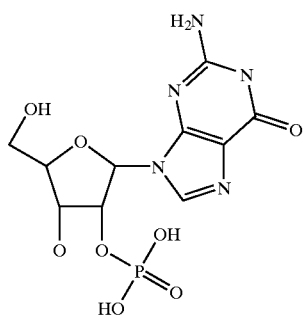

Guanosine 3'-monophosphate

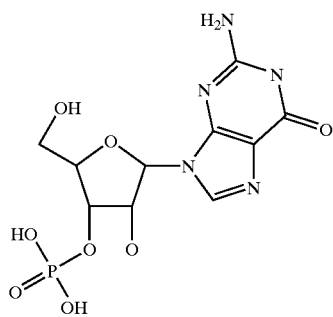

Guanosine 5'-monophosphate

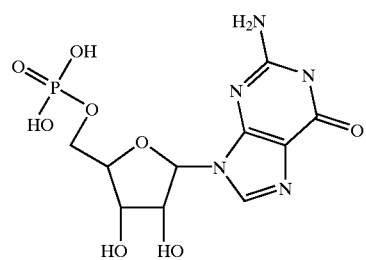

Uridine 5'-monophosphate

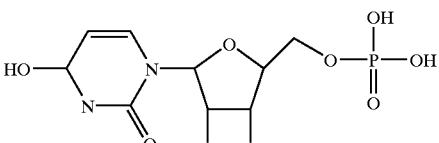

2'-deoxyadenosine 5'-monophosphate

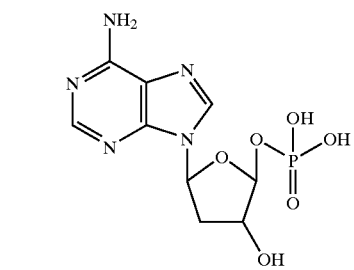

2'-deoxycytidine 5'-monophosphate

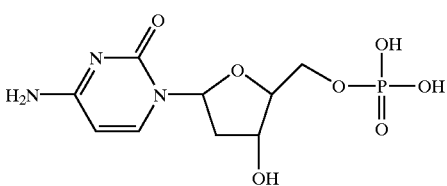

2'-deoxyguanosine 5'-monophosphate

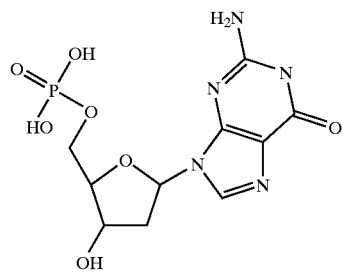

2'-deoxyadenosine 5'-triphosphate

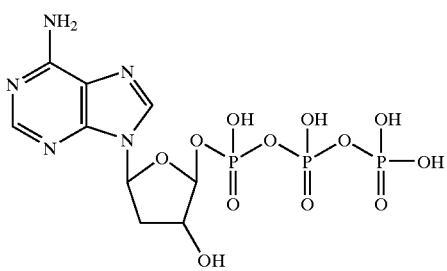

Accordingly, the present invention provides for compositions comprising bitterness inhibitors. Bitterness inhibitors, such as those described herein are commercially available (Sigma Chemical Co.; St.Louis, Mo.). Such compositions include any substances which may come in contact with taste tissue of a subject, including but not limited to foods, pharmaceuticals, dental products, cosmetics, and wetable glues used for envelopes and stamps.

In one set of embodiments, a bitterness inhibitor is used to counteract the perception of bitterness associated with a co-present bitter tastant. In these embodiments, a composition of the invention comprises a bitter tastant and a bitterness inhibitor, where the bitterness inhibitor is present at a concentration which inhibits bitter taste perception. For example, when the concentration of bitter tastant in the composition and the concentration of bitterness inhibitor in the composition are subjected to an assay as disclosed herein, the bitterness inhibitor inhibits the activation of G-protein by the bitter tastant.

Suitable bitterness inhibitors include, but are not limited to, adenosine 3':5'-cyclic monophosphate, guanosine 2':3'-cyclic monophosphate, guanosine 3':5'-cyclic monophosphate, cytidine 5'-monophosphate, guanosine 2'-monophosphate, guanosine 3'-monophosphate, guanosine 5'-monophosphate, uridine 5'-monophosphate, 2'-deoxyadenosine 5'-monophosphate, 2'-deoxyadenosine 5'-triphosphate, 2'-deoxycytidine 5'-monophosphate, and 2'-deoxyguanosine 5'-monophosphate. The amount of bitterness inhibitor added to a composition comprising a bitter tastant may vary depending on the amount of bitter tastant present, other compounds present in the composition, and the species of animal intended to taste the composition. In specific, non-limiting embodiments of the invention, the bitterness inhibitor may be present at a concentration between about 0.01 and 20 mM.

In specific, non-limiting embodiments, where adenosine 3':5'-cyclic monophosphate is used as the bitterness inhibitor, a composition comprising a bitter tastant may further comprise a concentration of adenosine 3':5'-cyclic monophosphate of between about 0.01 and 10 mM, preferably between about 0.1 and 5 mM.

In specific, non-limiting embodiments, where guanosine 2':3'-cyclic monophosphate is used as the bitterness inhibitor, a composition comprising a bitter tastant may further comprise a concentration of guanosine 2':3'-cyclic monophosphate of between about 0.1 and 20 mM, preferably between about 1 and 10 mM.

In specific, non-limiting embodiments, where guanosine 3':5'-cyclic monophosphate is used as the bitterness inhibitor, a composition comprising a bitter tastant may further comprise a concentration of guanosine 3':5'-cyclic monophosphate of between about 0.1 and 20 mM, preferably between about 1 and 10 mM.

In specific, non-limiting embodiments, where cytidine 5' monophosphate is used as the bitterness inhibitor, a composition comprising a bitter tastant may further comprise a concentration of cytidine 5' monophosphate of about 0.1 and 20 mM, preferably between about 1 and 10 mM.

In specific, non-limiting embodiments, where guanosine 2' monophosphate is used as the bitterness inhibitor, a composition comprising a bitter tastant may further comprise a concentration of guanosine 2' monophosphate of between of about 0.1 and 20 mM, preferably between about 1 and 10 mM.

In specific, non-limiting embodiments, where guanosine 3' monophosphate is used as the bitterness inhibitor, a composition comprising a bitter tastant may further comprise a concentration of guanosine 3' monophosphate of between about 0.1 and 20 mM, preferably between about 1 and 10 mM.

In specific, non-limiting embodiments, where guanosine 5' monophosphate is used as the bitterness inhibitor, a composition comprising a bitter tastant may further comprise a concentration of guanosine 5' monophosphate of between about 0.1 and 10 mM, preferably between about 1 and 10 mM.

In specific, non-limiting embodiments, where uridine 5' monophosphate is used as the bitterness inhibitor, a composition comprising a bitter tastant may further comprise a concentration of uridine 5' monophosphate of between about 0.01 and 10 mM, preferably between about 0.1 and 5 mM.

In specific, non-limiting embodiments, where 2' deoxyadenosine 5' monophosphate is used as the bitterness inhibitor, a composition comprising a bitter tastant may further comprise a concentration of 2' deoxyadenosine 5' monophosphate of between about 0.01 and 10 mM, preferably between about 0.1 and 5 mM.

In specific, non-limiting embodiments, where 2'-deoxyadenosine 5'-triphosphate is used as the bitterness inhibitor, a composition comprising a bitter tastant may further comprise a concentration of 2'-deoxyadenosine 5'-triphosphate of about 0.01 and 10 mM, preferably between about 0.1 and 5 mM.

In specific, non-limiting embodiments, where 2' deoxycytidine 5'-monophosphate is used as the bitterness inhibitor, a composition comprising a bitter tastant may further comprise a concentration of 2' deoxycytidine 5' monophosphate of between about 0.1 and 10 mM, preferably between about 1 and 10 mM.

In specific, non-limiting embodiments, where 2' deoxyguanosine 5'-monophosphate is used as the bitterness inhibitor, a composition comprising a bitter tastant may further comprise a concentration of 2' deoxyguanosine 5'-monophosphate of between about 0.01 and 10 mM, preferably between about 0.1 and 5 mM.

The present invention may be used to improve the taste of foods by decreasing or eliminating the aversive effects of bitter tastants. If a bitter tastant is a food preservative, the inhibitors of the invention may permit or facilitate its incorporation into foods, thereby improving food safety. For foods administered as nutritional supplements, the incorporation of inhibitors of the invention may encourage ingestion, thereby enhancing the effectiveness of these compositions in providing nutrition or calories to a subject.

The inhibitors of the invention may be incorporated into medical and/or dental compositions. Certain compositions used in diagnostic procedures have an unpleasant taste, such as contrast materials and local oral anesthetics. The inhibitors of the invention may be used to improve the comfort of subjects undergoing such procedures by improving the taste of compositions. In addition, the inhibitors of the invention may be incorporated into pharmaceutical compositions, including tablets and liquids, to improve their flavor and improve patient compliance particularly where the patient is a child or a non-human animal).

The inhibitors of the invention may be comprised in cosmetics to improve their taste features. For example, but not by way of limitation, the inhibitors of the invention may be incorporated into face creams and lipsticks.

In addition, the inhibitors of the invention may be incorporated into compositions that are not traditional foods, pharmaceuticals, or cosmetics, but which may contact taste membranes. Examples include, but are not limited to, soaps, shampoos, toothpaste, denture adhesive, and glue on the surfaces of stamps and envelopes.

The preferred embodiment of the invention is such that the bitter blocking compounds claimed are nucleotides in the form of adenosine, guanosine, cytodine, thymidine and uridine or their derivatives and contain an ionizable phosphate or similar anionic organic molecule. The bitter composition of the present invention include, but are not limited to, bitter pharmaceutical alkaloids such as acetaminophen, ampicillin, chlorpheniramine, chlarithromycin, doxylamine, guaifenesin, ibuprofen, pseudoephidrine hydrochloride, and ranitidine, bitter pharmaceutical metallic salts such as zinc containing bioadhesives (denture adhesive), bitter vitamins, bitter components of foods such as creatine, limonin, naringin, quinizolate, and bitter components of beverages such as caffeine, humulone. The bitter composition and blocker are in a pharmaceutically acceptable matrix in which the matrix has a composition such that the pH range is between 5.0 and 8.0. The expression "pharmaceutically acceptable matrix" includes solid tablets, chewable matrices such as gums, fast dissolving matrices, semi solid granules, liquid carriers, liquid sprays. These matrices are prepared by utilizing any one of a wide variety of different prior arts methods well known to one of ordinary skill in the art.

The amount of blocking agent used will vary depending upon the dosage requirements of the particular bitter compound. Generally, the amount of bitter compound will range from about 0.1% to 90% by weight.

The concentration of the bitter blocking compounds claimed is in the range of 0.01 mM to 20 mM and will vary depending on the amount of bitter compound used and its bitterness.

The compositions as described above are sufficient to block the bitter characteristics of the compounds described herein as determined by decrease in the level of transducin activation in the in vitro assay or by subjectively decreasing the perception of bitter taste in the in vivo assay.

It may be desirable to add excipients to the composition. These excipients may include bulking agents, binders, stabilizers, plasticizers, pigments, flavorants, sweeteners and the like.

The bitter blocking compounds claimed may be incorporated into pharmaceutical, food, beverage and cosmetic compositions to decrease the bitterness of these compositions. In addition, the bitter blocking compounds claimed may be incorporated into compositions that may contact taste tissue. Such examples include, but are not limited to, cosmetics. denture adhesive, shampoo, soap, toothpaste, and toxic compositions used in pest control.

6. EXAMPLE

Identification of Bitterness Inhibitors

The data presented below describes the identification of various nucleotide compounds having bitterness inhibitory activity. Previously, it has been shown that membranes isolated from bovine circumvallate papillae activate transducin in response to bitter compounds (Ruiz-Avila et al., 1995 Nature 376:80–5). The heterotrimeric guanine nucleotide binding protein (G protein) transducin is an ideal reporter enzyme of bitter taste signal transduction because it can be highly purified (>95%), in large quantities (5–10 mg/200 retina). Furthermore, transducin has a very low level of basal activity, and in conjunction with nonhydrolyzable GTP analogues, can generate activated species which are readily measured by guanine radionucleotide binding.

The G effect was initially defined as the binding of GTP upon stimulation of tissue with a ligand (Rodbell et al., 1971 J. Biol. Chem. 246:1877–82). It is now known that these ligands activate seven-transmembrane-helical G protein coupled receptors, which catalyze the exchange of GTP for bound GDP in the α-subunit of heterotrimeric G proteins. Thus, transducin activation by bitter stimulated taste membranes may be measured by uptake of GTP.

Since G proteins have an intrinsic GTPase activity, which terminates the activation cycle, a radioactive nonhydrolyzable analogue of GTR such as [$^{35}$S] GTPγS or [$^{3}$H] GppNHp must be used. To test for the inhibitory activity of nucleotide compounds, several modifications of the standard [$^{35}$S] GTPγS binding assay were made to efficiently measure activation by bitter responsive receptors that couple to gustducin or transducin (Gravina et al., in preparation). To maximize the bitter dependent change in radiolabel uptake GDP:GTPγS ratios, buffer composition, and specific activity of the [$^{35}$S] GTPγS were adjusted. Ruiz-Avila et al. demonstrated taste membrane dependent activation of exogenously added transducin by bitter tastants in trypsin digest assays (Ruiz-Avila et al., 1995 Nature 376:80–5; Ruiz-Avila et al, 2000 Chem Senses 25:361–8).

Radionucleotide bound to transducin can be measured by filter binding followed by washing to remove unbound label (Asano et al., 1984 Biochemistry 23:5460–5467). The final concentrations in the [$^{35}$S] GTPγS binding assay mix are 10 mM HEPES pH 7.5, 5 mM $MgCl_2$, 50 mM NaCl, 1 mM dithiolthreitol, 10 μM GDP, 1 μM [$^{35}$S] GTPγS (0.1 μCi/sample), 0.5 μg/0.05 ml transducin heterotrimer. A 2× stock of the above mixture is added to the bitter compound. Reactions are started by addition of 5 μg/0.05 ml bovine circumvallate membranes and the sample volume is adjusted to 0.05 ml with water. Samples are incubated at room temperature (25±2° C. for 2 hours). Long incubation times are necessary due to the low density of receptors in the membranes. Similar results are obtained with high dilutions of rhodopsin. Samples are then filtered through BA-85 nitrocellulose filters and washed 3 times with 3 ml of 50 mM Tris-HCl pH 7.5, 4 mM $MgCl_2$, and 0.1 M NaCl. Filters are dried, placed in scintillation fluid and the radioactivity is determined by scintillation counting. Experiments are performed in triplicate with several concentrations of the tastant of interest. Controls include: (i) a rhodopsin positive control, (ii) a no tastant negative control and (iii) a no membrane control +/−tastants.

This assay can measure activation of transducin by bitter compounds in the presence of taste membrane. Results in FIG. 1A show that transducin had minimal binding of [$^{35}$S] GTPγS in the absence of membranes or when membranes were boiled for 5 min. Although circumvallate membranes alone stimulated [$^{35}$S] GTPγS binding, denatonium (10 mM) significantly (p>0.002; Student's t-test) increased radiolabel binding. This activation was ~40% of the maximal achieved with rhodopsin stimulated [$^{35}$S] GTPγS binding and was shown to be time dependent. Similar basal background levels were observed previously (Ming et al., 1999 Proc Natl Acad Sci USA 96:9903–8). FIG. 1B shows the concentration dependent activation of transducin by denatonium in the presence of circumvallate membranes. These data show apparent saturation of transducin activation, a hallmark of receptor dependency. Over 50% of bitter tastants tested give a positive response by this method.

Data is presented in FIGS. 2A–K showing that a number of nucleotides decrease the in vitro response of transducin to compounds perceived as bitter.

The in vivo taste assay identifies the bitter blockers that are claimed by testing their activity using human subjects. A concentration of the bitter compound quinine in water was found that the subject rated as 5 for bitterness on a scale of 0 to 10, where 0 is no bitterness and 10 is the most intense bitterness the subject has ever encountered. This concentration of quinine was then made up containing 10 mM of the nucleotide to be tested and the subject rated the bitterness of this solution on the same scale. Results are presented for CMP and dATP (FIG. 3).

The present invention is not to be limited in scope by the specific embodiments described herein which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the claims. Various publications are cited herein, the contents of which are hereby incorporated, by reference, in their entireties.

We claim:

1. A composition comprising a bitter tastant selected from the group comprising foods and beverages, and a bitterness inhibitor, wherein said bitterness inhibitor is uridine 5'-monophosphate and the inhibitor is present at a concentration which inhibits bitterness.

2. A composition comprising a bitter tastant selected from the group comprising foods and beverages, and a bitterness inhibitor, wherein said bitterness inhibitor is a purine or pyrimidine group, or derivative thereof, and ionizable phosphate or other anionic organic molecule and the inhibitor is present at a concentration which inhibits bitterness.

3. A method of inhibiting the perception of a bitter taste of a food or beverage in a subject comprising administering to the subject an effective amount of a bitterness inhibitor wherein said inhibitor is uridine 5'-monophosphate.

4. A method of inhibiting the perception of a bitter taste of a food or beverage in a subject comprising administering to the subject an effective amount of a bitterness inhibitor wherein said inhibitor is a purine or pyrimidine group, or derivative thereof, and ionizable phosphate or other anionic organic molecule.

5. A composition consisting essentially of a bitter tastant selected from the group comprising foods and beverages, and a bitterness inhibitor, wherein said bitterness inhibitor is uridine 5'-monophosphate and the inhibitor is present at a concentration which inhibits bitterness.

6. A method of inhibiting the perception of a bitter taste of a food or beverage in a subject, said method consisting essentially of administering to the subject an effective amount of a bitterness inhibitor in a composition which consisting essentially of a bitter tastant and bitterness inhibitor wherein said inhibitor is uridine 5'-monophosphate.

7. A method of inhibiting the perception of a bitter taste of a food or beverage in a subject consisting essentially of administering to the subject an effective amount of a bitterness inhibitor in a composition which consists essentially of a bitter tastant and bitterness inhibitor wherein said inhibitor is a purine or pyrimidine group, or derivative thereof, and ionizable phosphate or other anionic organic molecule.

8. The composition of claim 1, wherein said bitter tastant consists essentially of a bitter food, wherein said bitterness inhibitor is uridine 5'-monophosphate and the inhibitor is present at a concentration which inhibits bitterness.

9. The composition of claim 1, wherein said bitter tastant consists essentially of a bitter beverage, wherein said bitterness inhibitor is uridine 5'-monophosphate and the inhibitor is present at a concentration which inhibits bitterness.

* * * * *